United States Patent
Mosler et al.

[11] Patent Number: 6,099,572
[45] Date of Patent: Aug. 8, 2000

[54] RESILIENT FOOT INSERT

[75] Inventors: Lueder Mosler; Martin Pusch, both of Duderstadt, Germany

[73] Assignee: Otto Bock Orthopaedishche Industrie Besitz- Und Verwaltungs-Kommandit- Gesellschaft, Duderstadt, Germany

[21] Appl. No.: 09/064,094

[22] Filed: Apr. 22, 1998

[30] Foreign Application Priority Data

Apr. 24, 1997 [DE] Germany ................. 297 07 416 U

[51] Int. Cl.⁷ ............................. A61F 2/66; A61F 2/68
[52] U.S. Cl. ............................... 623/53; 623/55; 623/52
[58] Field of Search ...................... 623/52, 53, 50, 623/27, 54, 55, 56

[56] References Cited

U.S. PATENT DOCUMENTS

| | | | |
|---|---|---|---|
| 4,959,073 | 9/1990 | Merlette | 623/55 |
| 5,139,525 | 8/1992 | Kristinsson | 623/55 |
| 5,156,632 | 10/1992 | Wellershaus | 623/55 |
| 5,181,933 | 1/1993 | Phillips | 623/55 |
| 5,258,039 | 11/1993 | Goh et al. | 623/55 |
| 5,290,319 | 3/1994 | Phillips | 623/55 |
| 5,509,938 | 4/1996 | Phillips . | |
| 5,514,185 | 5/1996 | Phillips | 623/52 |
| 5,549,714 | 8/1996 | Phillips | 623/55 |
| 5,766,265 | 6/1998 | Phillips | 623/55 |
| 5,800,570 | 9/1998 | Collier | 623/55 |
| 5,897,594 | 4/1999 | Martin et al. | 623/55 |

FOREIGN PATENT DOCUMENTS

| | | |
|---|---|---|
| 498799 | 10/1922 | France . |
| 2 640 499 | 6/1990 | France . |
| 363938 | 12/1921 | Germany . |
| 4205900 | 3/1992 | Germany . |
| 40 37 928 | 5/1992 | Germany . |
| 40 38 063 | 6/1992 | Germany . |
| 42 05 899 | 9/1992 | Germany . |
| 42 05 900 | 9/1992 | Germany . |
| 42 08 941 | 9/1993 | Germany . |
| 93 15 665 | 1/1994 | Germany . |
| WO 96/04869 | 2/1996 | WIPO . |

*Primary Examiner*—David H. Willse
*Assistant Examiner*—Suzette J. Jackson
*Attorney, Agent, or Firm*—Foley & Lardner

[57] ABSTRACT

The invention relates to a resilient foot insert for an artificial foot, having at least one leaf spring. In order to increase structural strength, the at least one leaf spring comprises a plurality of leaf spring elements which are coupled in parallel, are arranged next to one another and are connected to one another at their two end regions. Between these two end regions, there is a clearance distance or gap between an adjacent pair of the leaf spring elements. An adjustable pressure buffer in the gap adjusts the deformation characteristics of the at least one leaf spring.

23 Claims, 3 Drawing Sheets

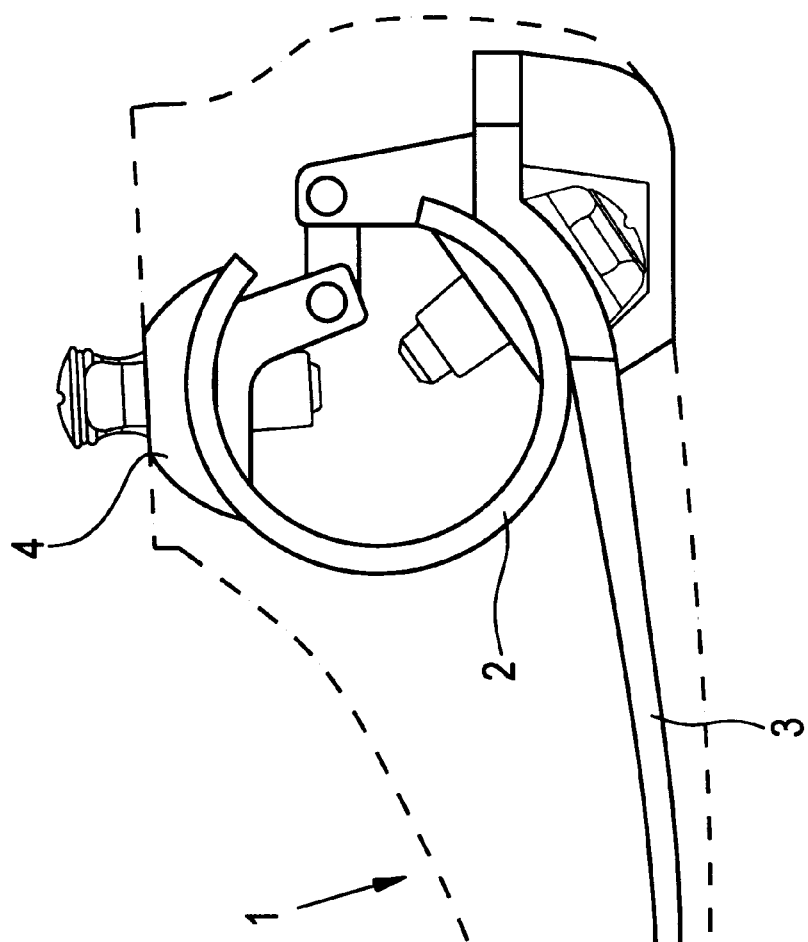
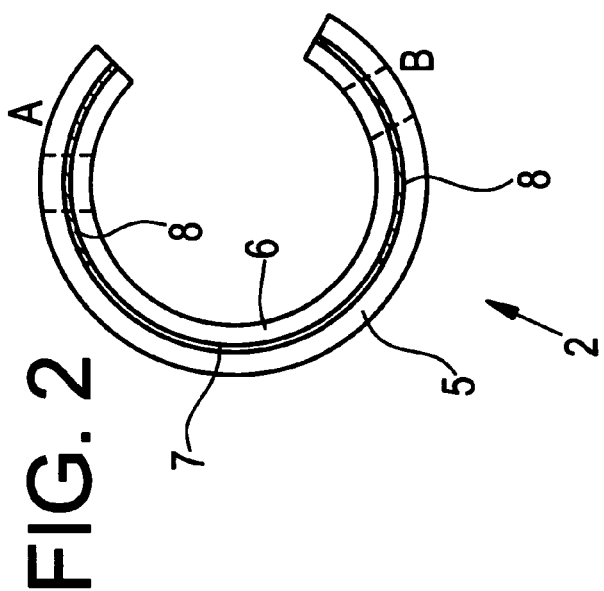

RESILIENT FOOT INSERT

BACKGROUND OF THE INVENTION

1. Field of the Invention

The present invention relates to a resilient foot insert for an artificial foot. In particular, the present invention relates to a resilient foot insert having at least one leaf spring.

2. Description of Related Art

Resilient foot inserts are disclosed, for example, in U.S. Pat. No. 4,959,073, German Patent Nos. 40 38 063 and 42 05 900, and French Patent No. 26 40 499, as well as in German Utility Model No. G 93 15 665.0.

The leaf springs used in foot inserts are subjected to extremely high loads. Conventional springs are made of carbon composite, titanium, or other suitable materials. The functionally required deformation leads to high stresses, and the fatigue strength of conventional leaf springs is often inadequate for absorbing these stresses.

SUMMARY OF THE INVENTION

One object of the present invention is to increase the structural strength of leaf springs used in resilient foot inserts. Another object of the present invention is to adjust the walking dynamics for the desired comfort preferences and activities of a user.

In accomplishing the foregoing objects there has been provided according to the present invention a resilient foot insert for an artificial foot. The resilient foot insert comprises at least one spring including a plurality of leaf spring elements coupled in parallel, the plurality of leaf spring elements being arranged next to one another and having first and second connections to one another at their respective end portions, at least one of the first and second connections being rigid with respect to torque, and the at least one spring further including a gap between an adjacent pair of the plurality of leaf spring elements in a region between the respective end portions. Preferably, a pressure buffer is in the gap between the adjacent pair of the plurality of leaf spring elements.

Similarly, the foregoing objects are also accomplished according to the present invention by providing a resilient foot insert for an artificial foot having a cosmetic covering simulating the appearance of a foot. The resilient foot insert comprises a forefoot spring including a plurality of leaf spring elements coupled in parallel, the plurality of leaf spring elements being arranged next to one another and having first and second connections to one another at their respective end portions, at least one of the first and second connections being rigid with respect to torque, and the forefoot spring further including a gap between an adjacent pair of the plurality of leaf spring elements in a region between the first and second end portions; a pressure buffer in the gap between the adjacent pair of the plurality of leaf spring elements; and a C-shaped heel spring having an upper portion connected to a rear end of the forefoot spring and a lower portion being movable with respect to the upper portion for adjusting the pressure buffer with respect to the forefoot spring.

Additional objects, features and advantages of the invention will be set forth in the description which follows, and in part will be obvious from the description, or may be learned by practice of the invention.

BRIEF DESCRIPTION OF THE DRAWINGS

The accompanying drawings, which are incorporated in and constitute a part of the specification, illustrate presently preferred embodiments of the invention, and, together with the general description given above and the detailed description of the preferred embodiments given below, serve to explain the principles of the invention.

FIG. 1 shows a resilient foot insert for an artificial foot, indicated by chain-dotted lines, in a longitudinal vertical plane of the prothesis.

FIG. 2 shows a modified embodiment of a detail from FIG. 1.

DETAILED DESCRIPTION OF THE PREFERRED EMBODIMENTS

Figure 3:
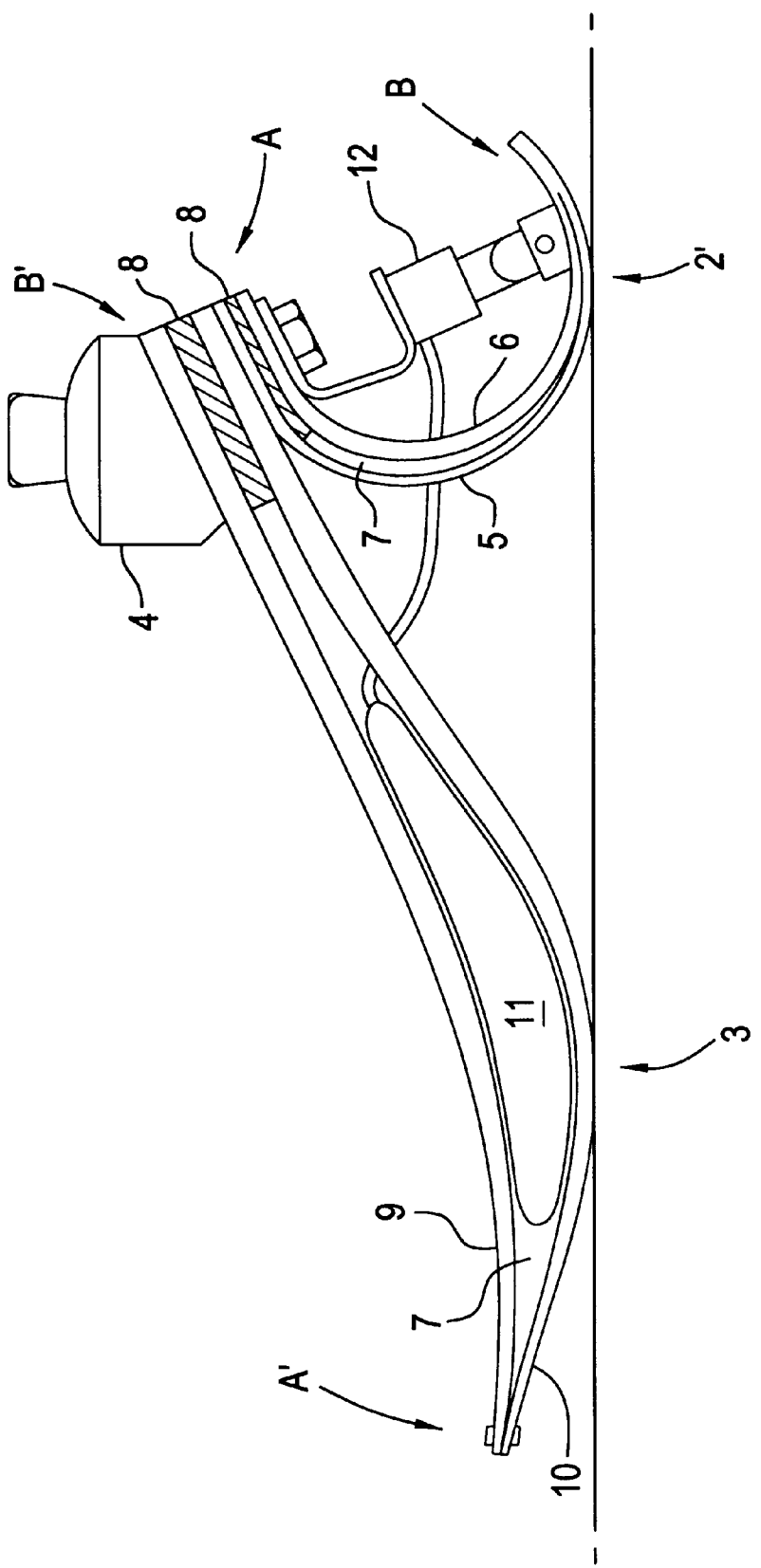
FIG. 3 shows a modified embodiment of a pneumatically self-adjusting artificial foot.

Simple material reinforcement has generally been unable to increase structural strength without negatively impacting spring characteristics. However, the present inventors have discovered that parallel coupling of two softer springs provides unexpected structural strength without adversely affecting the desired spring characteristics.

Depending on the shape and characteristics of the leaf spring elements, there must be a sufficient clearance distance, or gap, between the two leaf spring elements in order to ensure that during deformation of the leaf spring, premature contact of the leaf spring elements on one another is prevented. This avoids abrupt changes in the spring characteristic.

To achieve the necessary fatigue strength, preferred embodiments of the present invention provide a spacer element at least in one of the two end regions between the two leaf spring elements.

According to preferred embodiments of the present invention, the total strength of the foot insert is further improved if the two leaf spring elements forming a forefoot spring have, in the clearance distance formed between the leaf spring elements, a pressure buffer which can either be resilient or be a rigid spacer element. More preferably, the pressure buffer can be exchanged for another pressure buffer having a different size, shape or strength, or having different spring characteristics. The physical and spring characteristics can also be modified by displacing a mechanical spacer element in the longitudinal direction of the leaf spring elements.

According to preferred embodiments of the present invention, in order to be able to improve total strength, the clearance distance between the two leaf spring elements forming the forefoot spring is controlled. According to more preferred embodiments of the present invention, this control function regulates the strength setting as a function of the walking dynamics of the user. According to preferred embodiments of the present invention, the pressure buffer can be an air-filled pressure cushion which, in an initially filled state, bears without stress on the two leaf spring elements forming the forefoot spring, i.e. does not pre-stress the leaf springs. To control such an air-filled pressure cushion, the pressure cushion is connected to the pressure attachments of an air pump element which is incorporated together with the foot insert into the artificial foot and can be actuated as a function of the patient's weight and/or by the patient's activity. According to more preferred embodiments of the present invention, the air pump element is fitted between the branches, or arm portions, of a C-shaped heel spring in such a way that its working stroke corresponds to the elastic deformation of the heel spring. Since the spring deformations of the heel are generally considerably smaller than those of the forefoot, the influence of the heel deformation on the user's gait pattern is minimal. According to preferred embodiments of the present invention, heel deformation is used to control the forefoot strength whereby the aforementioned air pump element can be actuated in response to compression of the heel spring.

The walking dynamics of the user depend on how they want to feel, i.e. their comfort preferences, and also on what they are doing at a given time. Whereas the function of adjusting how the patient feels is entirely possible by means of a successively adjusting system (as described above with regard to an air cushion), the adjustment to what the patient is doing at a given time (for example at the workplace) must be effected very quickly, in practice from one step to the next. However, conventional pneumatic systems are not able to provide rapid adjustment of this kind.

To permit a rapid, automatic adjustment of the prosthetic foot to the actual walking dynamics of the user, it is proposed, according to preferred embodiments of the present invention, for the longitudinal displacement of the pressure buffer, designed as rigid spacer element, between the leaf spring elements forming the forefoot spring, to be derived mechanically from the strength of the heel tread. According to one preferred embodiment of the present invention, a C-shaped heel spring is connected to the forefoot spring via its upper branch under the rear end region of the forefoot spring, and, at its lower free branch end, is connected to the pressure buffer via a push rod in such a way that when the heel spring is compressed by the user, the push rod displaces the pressure buffer in the direction toward the front end region of the forefoot spring. If the user steps briskly and firmly on the heel, the push rod pushes the spacer element further forward. During the succeeding loading of the forefoot, the position of the spacer element is fixed. The user can then take a longer step by means of the more rigid forefoot lever than would be possible with a softer forefoot lever. After unloading of the forefoot, the fixed positioning of the spacer element is released and the spacer element can return to its starting position. An arrangement of this kind permits adjustment of the forefoot spring hardness for each individual step, which is advantageous in the case of greatly varying activities.

The jointless artificial foot illustrated in FIG. 1 has a cosmetic covering 1, indicated by dot-and-dash lines, which encloses a resilient foot insert.

The resilient foot insert according to one preferred embodiment of the present invention comprises a C-shaped spring 2 whose lower branch is screwed to the rear end of a base spring or forefoot spring 3. The upper branch of the C-shaped spring 2 is screwed to an adapter 4 via which the artificial foot can be connected to a leg prosthesis.

As shown in FIG. 2, the C-shaped spring 2 may comprise two leaf spring elements 5,6 which are coupled in parallel, are arranged next to one another, run approximately parallel to one another, and are connected to one another at their two end regions A,B and, between these two end regions, have a clearance distance 7 between one another. A spacer element 8 is provided in each case between the two leaf spring elements 5,6 at these two end regions A,B.

FIG. 3 shows a modified embodiment of a resilient foot insert according to a preferred embodiment of the present invention. This embodiment comprises a C-shaped heel spring 2' which is screwed via its upper branch to a forefoot spring 3, under the rear end region B of said forefoot spring 3. The forefoot spring 3 is made up of two leaf spring elements 9,10 which are coupled in parallel, are arranged next to one another, and are rigidly connected to one another in terms of torque at their two end regions A,B. In this case a spacer element 8 is only provided in the rear end region B between the two leaf spring elements 9,10. Between the two end regions A,B, the two leaf spring elements 9,10 have a clearance distance 7 between one another, into which a resilient pressure buffer 11 is fitted which bears without stress on the two leaf spring elements 9, 10.

According to the preferred embodiment of the present invention illustrated in FIG. 3, the pressure buffer 11 is an air-filled pressure cushion which is connected to the pressure attachments of an air pump element 12 which is incorporated together with the resilient foot insert 2,3 in the artificial foot and can be actuated as a function of the user's weight and/or by the user's activity. The air pump element 12 is fitted between the branches of the heel spring 2' in such a way that upon loading of the heel, that is to say upon compression of the heel spring 2', the air pump element 12 is activated and forces air into the pressure buffer 11.

Figure 4:
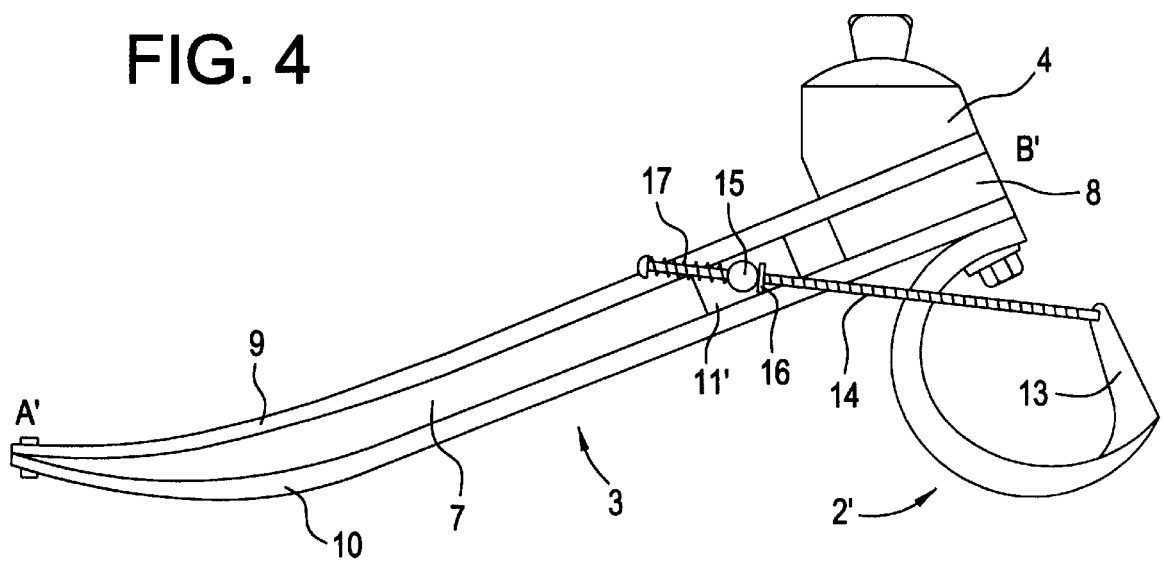
FIG. 4 shows a modified embodiment of a mechanically self-adjusting artificial foot.

In the preferred embodiment of the present invention according to FIG. 4, the heel spring 2' and the forefoot spring 3 essentially correspond to those in FIG. 3. However, instead of pneumatic adjustment, FIG. 4 illustrates mechanical adjustment. The lower free branch end 13 of the heel spring 2' is kinematically connected via a push rod 14 to a pressure buffer 11 comprising a rigid spacer element. The forward facing end of the push rod 14 is guided in a longitudinally displaceable manner through a crank 15 arranged laterally on the pressure buffer 11', and bears on a rear face of the crank 15 via a carrier 16. The free end of the push rod 14 is biased against the crank 15 via a spring 17. When the user steps briskly and firmly on the heel, the deformation of the heel spring 2' leads to a displacement of the push rod 14 which, via its carrier 16, displaces the pressure buffer 11' further forward, where it is fixed upon the subsequent loading of the forefoot. The spring 17 allows the heel spring 2' to spring back without altering the position of the pressure buffer 11'. After unloading of the forefoot, the spacer element is released, and then returns to its starting position under the effect of the weakly configured spring 17.

Thus, according to the present invention, a rapid, automatic adjustment of the prosthetic foot corresponding to the actual walking dynamics of the user is achieved. The strength of the two-layer forefoot spring being adjusted by means of a longitudinally displaceable, mechanical spacer element, which is controlled via the firmness of the heel tread.

Figure 5:
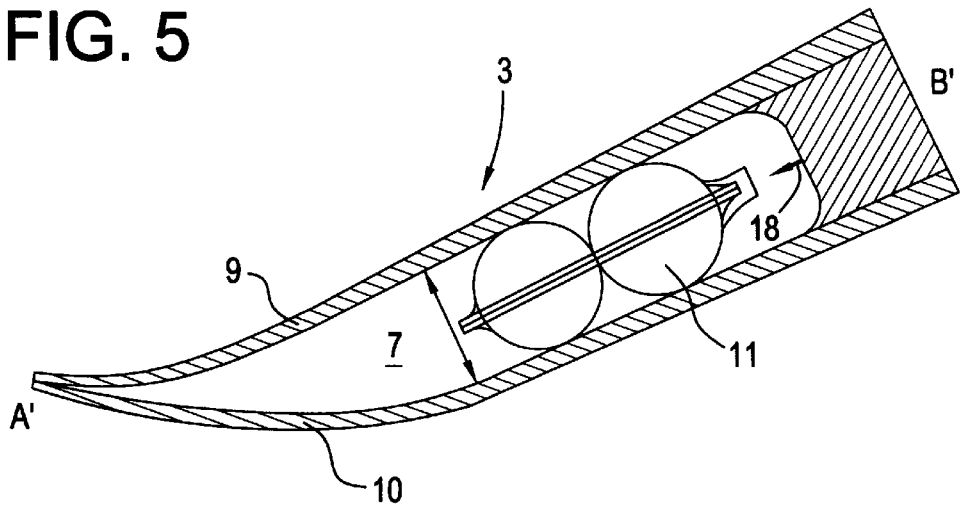
FIG. 5 shows a modified embodiment of a detail of a mechanically and pneumatically self-adjusting artificial foot.

FIG. 5 shows a forefoot spring 3 which, in the clearance distance 7 between its two leaf spring elements 9,10, receives pressure buffers 11 which—as the arrow 18 indicates—are displaceable in the longitudinal direction of the forefoot spring and/or can be expanded or compressed.

Figure 6:
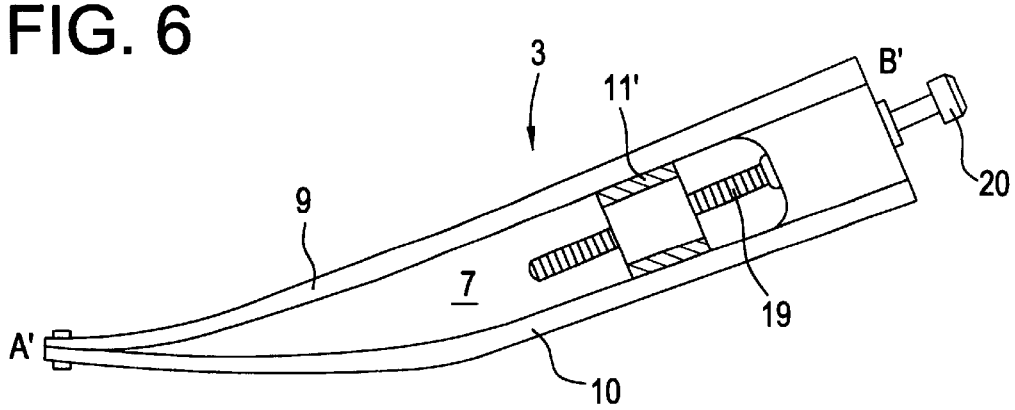
FIG. 6 shows a modified embodiment of a detail of a mechanically self-adjusting artificial foot.

FIG. 6 shows a forefoot spring 3 which is comparable to that in FIG. 5 and in which the pressure buffer 11', designed as a rigid spacer element, can be displaced longitudinally via an actuating member 19. This actuating member 19 is designed as a threaded spindle on which the pressure buffer 11' is guided via a spindle nut (not shown). The rear end of the spindle projects from the rear end region B of the forefoot spring 3 and can be manually actuated here via a knob 20.

Additional advantages and modifications will readily occur to those skilled in the art. Therefore, the invention in its broader aspects is not limited to the specific details, and representative devices, shown and described herein. Accordingly, various modifications may be made without departing from the spirit and scope of the general inventive concept as defined by the appended claims and their equivalents.

German Patent Application 297 07 416.4, filed Apr. 24, 1997, is hereby incorporated by reference.

What is claimed is:

1. A resilient foot insert for an artificial foot comprising:
   at least one spring element including a plurality of leaf spring elements coupled in parallel, said plurality of leaf spring elements being configured to be joined at the tip of the foot insert, said plurality of leaf spring elements being arranged next to one another and having first and second connections to one another at their respective end portions, at least one of said first and second connections being rigid with respect to torque, and said at least one spring further including a gap between an adjacent pair of said plurality of leaf spring elements in a region between said first and second end portions.

2. The resilient foot insert as claimed in claim 1, wherein said at least one spring further includes at least one spacer element between said adjacent pair of said plurality of leaf spring elements, each said at least one spacer element being proximate a respective end portion.

3. The resilient foot insert as claimed in claim 1, further comprising:
   a pressure buffer in said gap between said adjacent pair of said plurality of leaf spring elements.

4. The resilient foot insert as claimed in claim 3, wherein said pressure buffer comprises a resilient element.

5. The resilient foot insert as claimed in claim 4, wherein said pressure buffer comprises an air-filled resilient pressure cushion.

6. A resilient foot insert for an artificial foot, comprising:
   at least one spring element including a plurality of leaf spring elements coupled in parallel, said plurality of leaf spring elements being arranged next to one another and having first and second connections to one another at their respective end portions, at least one of said first and second connections being rigid with respect to torque, and said at least one spring further including a gap between an adjacent pair of said plurality of leaf spring elements in a region between said first and second end portions;
   a pressure buffer in said gap between said adjacent pair of said plurality of leaf spring elements, wherein said pressure buffer comprises an air-filled resilient pressure cushion; and
   an air pump element in fluid communication with said air-filled resilient pressure cushion, said air pump element and said at least one spring being adapted for enclosure within the artificial foot, and said air pump being responsive to the loading on the artificial foot.

7. The foot insert as claimed in claim 6, further comprising:
   a C-shaped heel spring connected to said at least one spring and having said air pump element extending between a top portion of said C-shaped heel spring and a lower portion of said C-shaped heel spring;
   wherein said air pump element is actuated as a function of compressing said C-shaped heel spring.

8. The resilient foot insert as claimed in claim 3, wherein said pressure buffer comprises a rigid spacer element.

9. A resilient foot insert for an artificial foot, comprising:
   at least one spring element including a plurality of leaf spring elements coupled in parallel, said plurality of leaf spring elements being arranged next to one another and having first and second connections to one another at their respective end portions, at least one of said first and second connections being rigid with respect to torque, and said at least one spring further including a gap between an adjacent pair of said plurality of leaf spring elements in a region between said first and second end portions;
   a pressure buffer in said gap between said adjacent pair of said plurality of leaf spring elements, wherein said pressure buffer comprises a rigid spacer element;
   a C-shaped heel spring having a top portion connecting to said at least one spring; and
   a push rod connecting said rigid spacer element to a lower portion of said C-shaped heel spring;
   wherein compression of said C-shaped heel spring displaces said rigid spacer element via said push rod, said rigid spacer element being longitudinally displaceable in said gap between said adjacent pair of said plurality of leaf spring elements.

10. The resilient foot insert as claimed in claim 3, wherein said pressure buffer is adapted to be exchanged for another pressure buffer having different characteristics.

11. The resilient foot insert as claimed in claim 3, wherein said pressure buffer is longitudinally displaceable in said gap between said adjacent pair of said plurality of leaf spring elements.

12. The resilient foot insert as claimed in claim 10, further comprising:
   an adjusting device adapted for longitudinally displacing said pressure buffer, wherein said adjusting device projects from between said adjacent pair of leaf spring elements, and wherein said adjusting device is manually actuated.

13. A resilient foot insert for an artificial foot having a cosmetic covering simulating the appearance of a foot, the resilient foot insert comprising:
   a forefoot spring including a plurality of leaf spring elements coupled in parallel, said plurality of leaf spring elements being arranged next to one another and having first and second connections to one another at their respective end portions, at least one of said first and second connections being rigid with respect to torque, and said forefoot spring further including a gap between an adjacent pair of said plurality of leaf spring elements in a region between said first and second end portions;
   a pressure buffer in said gap between said adjacent pair of said plurality of leaf spring elements; and
   a C-shaped heel spring having an upper portion connected to a rear end of said forefoot spring and a lower portion being movable with respect to said upper portion for adjusting said pressure buffer with respect to said forefoot spring.

14. The resilient foot insert as claimed in claim 13, further comprising:
   a push rod connecting said lower portion to said pressure buffer;
   wherein compression of said C-shaped heel spring displaces said pressure buffer via said push rod, said pressure buffer being displaced toward a front end of said forefoot spring.

15. The resilient foot insert as claimed in claim 14, further comprising:
a return spring biasing said pressure buffer to its normal position before said compression of said C-shaped heel spring.

16. The resilient foot insert as claimed in claim 15, wherein said return spring comprises a coil spring encircling said push rod and being interposed between a terminus of said push rod and said pressure buffer.

17. The resilient foot insert as claimed in claim 13, wherein said pressure buffer comprises an air-filled resilient pressure cushion.

18. The foot insert as claimed in claim 17, further comprising:
an air pump element in fluid communication with said air-filled resilient pressure cushion, said air pump element being actuated as a function of loading on the artificial foot;
wherein said air pump element, said pressure buffer, said forefoot spring and said C-shaped spring are enclosed within the cosmetic covering.

19. The foot insert as claimed in claim 18, wherein said air pump element extends between said top portion of said C-shaped heel spring and said lower portion of said C-shaped heel spring; and
wherein said air pump element is actuated as a function of elastically deforming said C-shaped heel spring.

20. A resilient foot insert for an artificial foot comprising:
at least one spring element including a plurality of leaf spring elements coupled in parallel, said plurality of leaf spring elements being arranged next to one another and having first and second rigid connections to one another at their respective end portions, at least one of said first and second connections being rigid with respect to torque, and said at least one spring further including at least one rigid spacer element between said adjacent pair of said plurality of leaf spring elements, said at least one spacer element being proximate to one of said first and second rigid connections, to define a clearance space between an adjacent pair of said plurality of leaf spring elements in a region between said first and second end portions.

21. A resilient foot insert as claimed in claim 20, wherein said at least one spring element has an approximately C-shaped configuration for placement in the heel portion of an artificial foot.

22. A resilient foot insert as claimed in claim 21, including two of said rigid spacer elements, each being proximate to one of said first and second rigid connections.

23. An artificial foot, comprising at least one resilient foot insert as claimed in claim 22, and a cosmetic covering simulating the appearance of a foot, said at least one leaf spring being enclosed in said cosmetic covering.

* * * * *